United States Patent [19]

Badolato et al.

[11] 4,160,801
[45] Jul. 10, 1979

[54] HEAT EXCHANGER-BLOOD OXYGENATOR COMBINATION

[75] Inventors: Anthony Badolato, Willingboro; Joseph S. Farrell, Piscataway, both of N.J.

[73] Assignee: Surgikos, New Brunswick, N.J.

[21] Appl. No.: 843,626

[22] Filed: Oct. 19, 1977

[51] Int. Cl.² .............................................. A61M 1/03
[52] U.S. Cl. ........................................ 422/46; 55/255; 55/256; 128/DIG. 3; 165/163; 261/DIG. 28; 422/47
[58] Field of Search ................... 23/258.5 R, 258.5 A, 23/258.5 BH, 258.5 MH; 55/255, 256; 261/DIG. 28; 195/1.8; 165/74, 163; 128/DIG. 3, 400

[56] References Cited

U.S. PATENT DOCUMENTS

| | | | |
|---|---|---|---|
| 1,946,118 | 2/1934 | Stockdale et al. | 165/163 X |
| 2,350,936 | 6/1944 | Smith | 165/163 X |
| 2,876,769 | 3/1959 | Cordova | 23/258.5 A |
| 2,896,620 | 7/1959 | Tremblay | 23/258.5 A |
| 3,130,780 | 4/1964 | Winship | 165/163 |
| 3,212,571 | 10/1965 | Romanos | 165/163 |
| 3,291,568 | 12/1966 | Sautter | 23/258.5 BH |
| 3,437,450 | 4/1969 | Greenwood | 23/258.5 A |
| 3,499,484 | 3/1970 | Lanzoni | 165/163 X |
| 3,615,238 | 10/1971 | Bentley et al. | 23/258.5 BH |
| 3,762,065 | 10/1973 | Wahlgren | 165/163 X |
| 3,768,977 | 10/1973 | Brumfeld et al. | 23/258.5 BH |
| 3,769,162 | 10/1973 | Brumfeld | 23/258.5 BH X |
| 3,915,650 | 10/1975 | Talonn et al. | 23/258.5 B |
| 3,960,657 | 6/1976 | Bowley | 23/258.5 BH X |
| 4,033,724 | 7/1977 | Tamiya | 23/258.5 BH |
| 4,058,369 | 11/1977 | Bentley et al. | 23/258.5 B |
| 4,065,264 | 12/1977 | Lewin | 23/258.5 BH |

Primary Examiner—Barry S. Richman
Attorney, Agent, or Firm—Irving Newman

[57] ABSTRACT

A blood treatment apparatus having within a sealed housing a chamber for mixing oxygen and blood, a column of packed beads through which the mixture of oxygen and blood passes to cause oxygenation of the blood, a blood defoamer through which the oxygenated blood must pass, a reservoir into which the defoamed blood passes and a heat-exchanger which occupies a substantial portion of the lower region of the reservoir. The heat-exchanger comprises a stacked array of spirally wound coils being connected at each of its ends to a manifold which is external of the sealed housing. The configuration of the various components and of the walls of the sealed housing are such that the coils provide high heat-exchange effectiveness by optimizing the size and uniformity of the spacing between coils through which the blood must pass.

10 Claims, 9 Drawing Figures

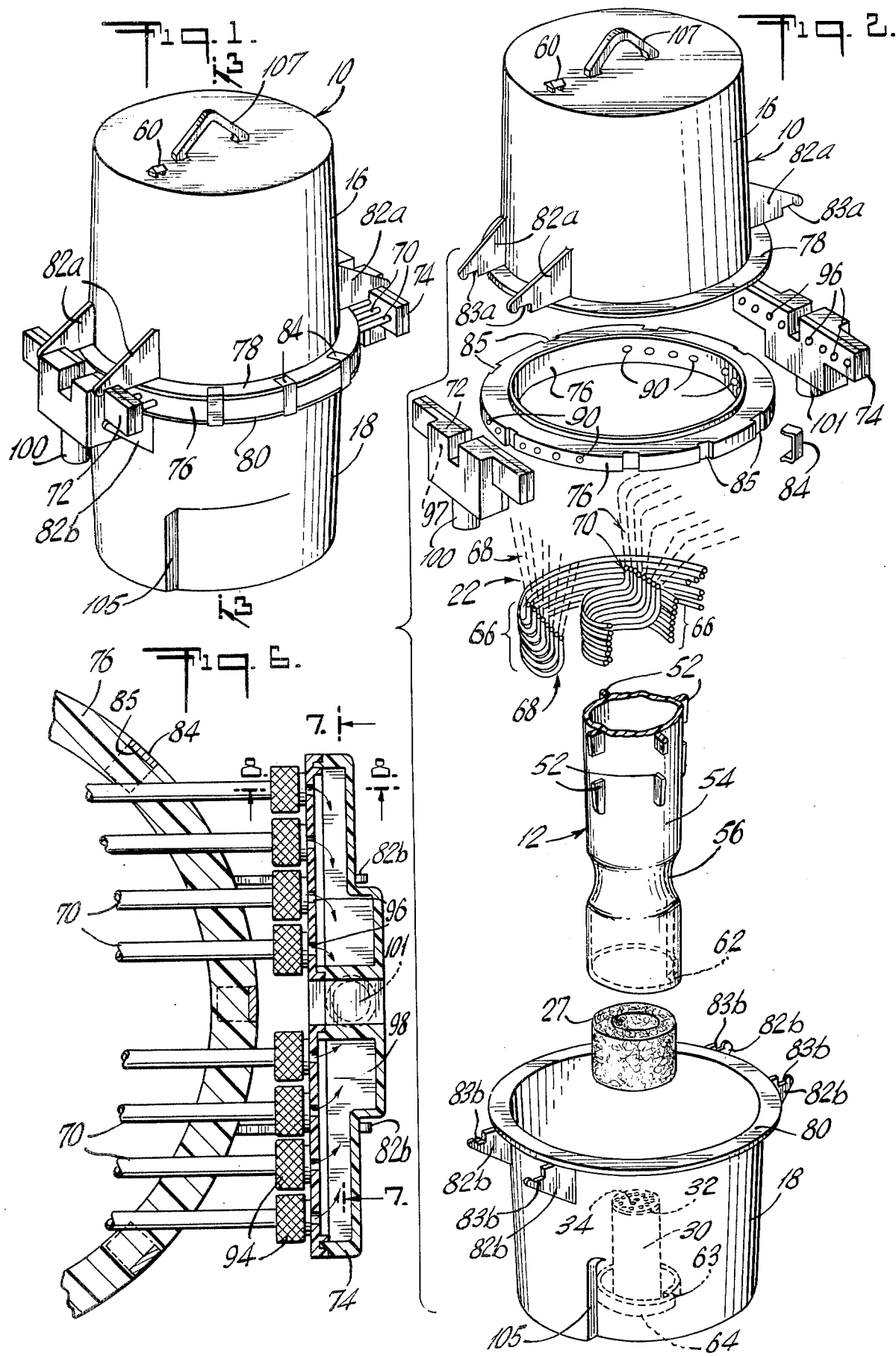

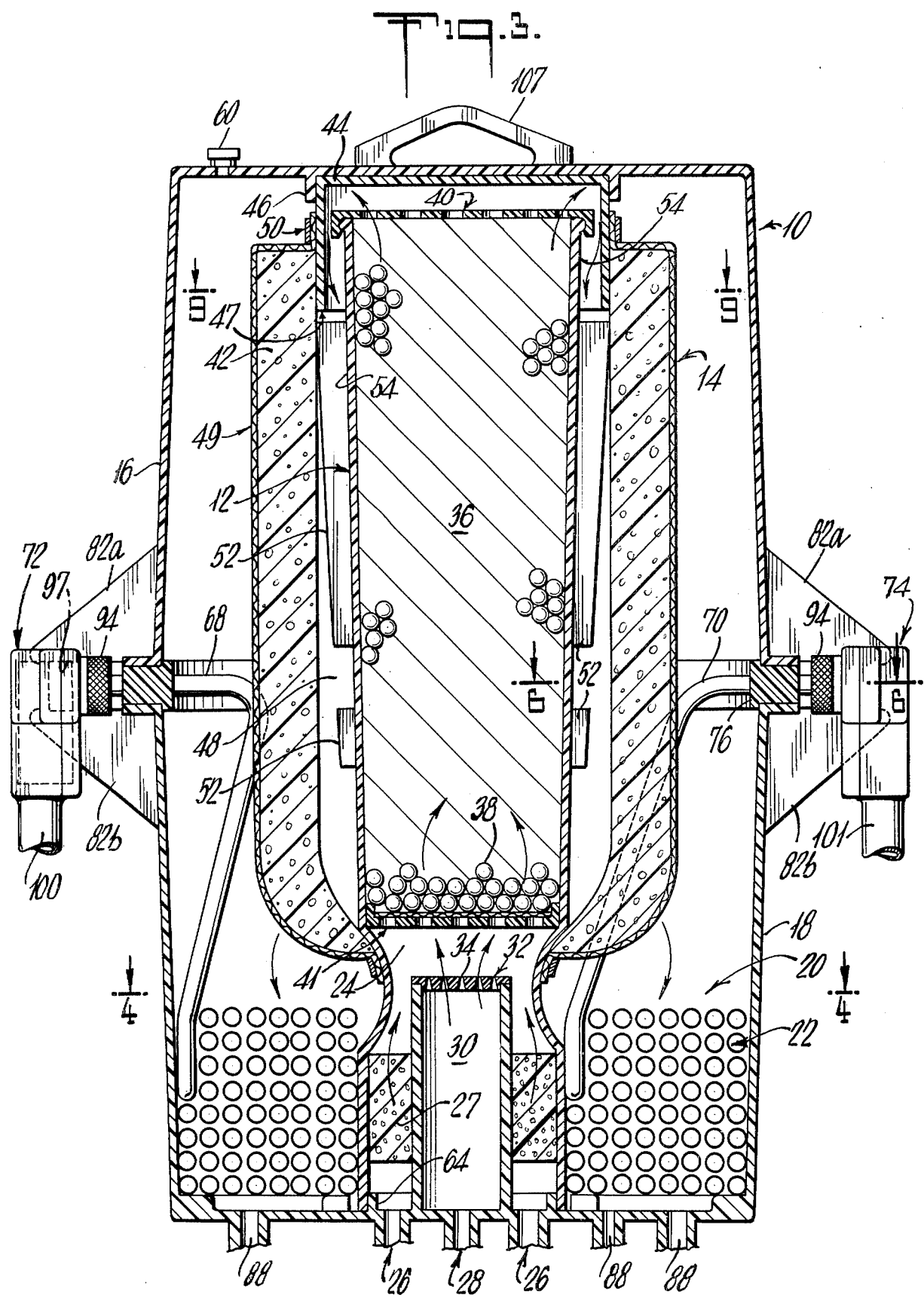

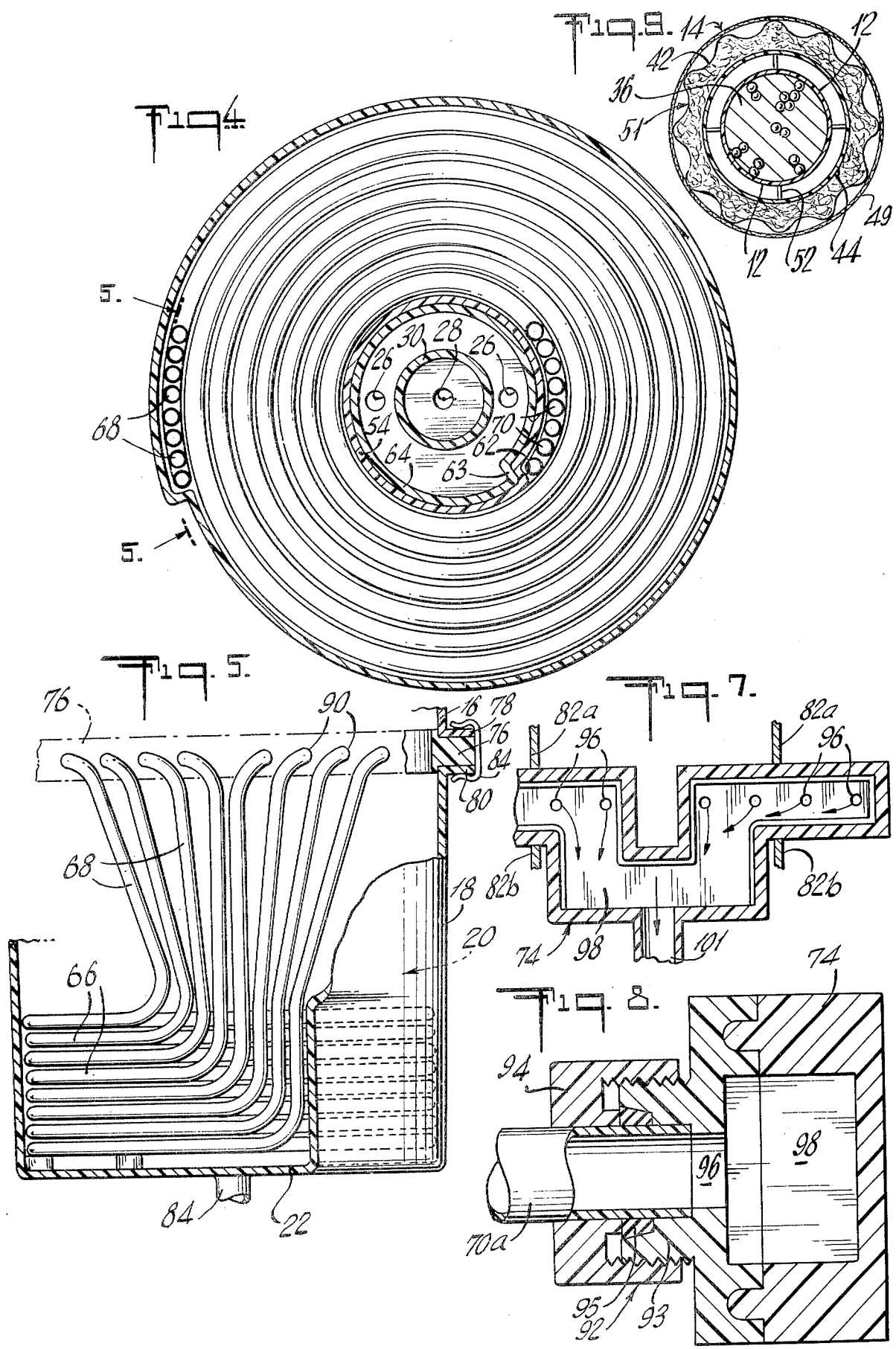

HEAT EXCHANGER-BLOOD OXYGENATOR COMBINATION

BACKGROUND OF THE INVENTION

1. Field of the Invention

This invention relates to blood treatment apparatus and, more particularly, it relates to artificial lungs and similar devices having heat-exchangers for accurately and rapidly regulating the temperature of the blood. A presently preferred embodiment of the present invention is a combination blood oxygenator and heat-exchanger unit affording advantageous economy, safety and compactness features.

2. Description of the Prior Art

Blood oxygenators are used in the course of cardio-pulmonary surgery and other procedures, when it is necessary to temporarily employ external mechanical means to perform the function of the lungs or of both the heart and lungs of a patient. It is important to carefully control the temperature of the blood during such procedures. Often the blood temperature is purposely lowered from normal body temperature to a preselected lower temperature during surgery. It is also necessary, at the surgeon's directions, to rapidly return the blood temperature to normal body temperature, while at the same time avoiding trauma to the blood (as by local contact overheating).

A number of prior art devices have been devised for carrying out these functions. Typical of such devices are those disclosed in U.S. Pat. Nos. 3,764,271; 3,769,162 and 3,768,977, as well as other patents discussed therein.

In general, the prior art heat exchanger devices suffer from one or more of the following disadvantages:

1. Relatively low heat exchange effectiveness due to one or more of (a.) insufficient heat-exchange surface for the volume of blood to be treated, (b.) poor flow design, (c.) poorly regulated blood film thickness at the heat exchange surface, or (d.) poor utilization of oxygenator/heat-exchanger design so as to maximize the contact time of the blood with the heat-exchange surface;

2. Danger of contamination of the patient's blood by direct contact with the heat-exchange fluid (typically, water) due to the presence of seals or similar potential leak sites separating the blood from the heat exchange fluid within the interior of the heat-exchange chamber. Such contamination of the blood can lead to serious injury or death of the patient;

3. The possibility of trauma to the blood due to one or more of (a.) turbulent flow, (b.) pockets of stagnation and (c.) flow barriers arising from the design of the equipment.

SUMMARY OF THE INVENTION

In accordance with one aspect of the present invention, we provide a blood treatment apparatus which overcomes the aforementioned drawbacks by utilizing, in combination with an oxygenator, a heat-exchanger having a plurality of coils for the heat-exchange fluid, each coil comprising a continuous spirally wound tube in a blood reservoir which surrounds an oxygenator chamber, the coils being vertically stacked, one on the other. The ends of the tubes lead to fluid inlet and outlet manifolds which are external thereto, so as to virtually eliminate the danger of contamination due to seal leakage.

In accordance with another aspect of the invention, each heat-exchange coil is positioned in a substantially horizontal plane within the blood reservoir and, because of the closely wound convolutions of the coil, occupies a substantial portion of the area of the reservoir within its respective plane. This promotes uniform, non-turbulent flow of blood across the coils and creates a relatively thin film of blood at the surfaces of the coils, so as to maximize heat-exchange efficiency. This configuration optimizes the use of heat-exchanger volume by providing maximum heat-exchange surface contact area for the volume of blood in the heat-exchanger.

BRIEF DESCRIPTION OF THE DRAWINGS

In the drawings:

FIG. 1 is a perspective view of a complete oxygenator/heat-exchanger device embodying the present invention;

FIG. 2 is an exploded perspective view, with parts broken away, of a portion of the components of the device of FIG. 1;

FIG. 3 is a vertical section taken on line 3—3 of FIG. 1;

FIG. 4 is a plan section taken on line 4—4 of FIG. 3;

FIG. 5 is a fragmentary section taken on line 5—5 of FIG. 4;

FIG. 6 is a fragmentary section taken on line 6—6 of FIG. 3;

FIG. 7 is a fragmentary section taken on line 7—7 of FIG. 6;

FIG. 8 is an enlarged section taken on line 8—8 of FIG. 6; and

FIG. 9 is a plan section taken on line 9—9 of FIG. 3.

DESCRIPTION OF THE PREFERRED EMBODIMENT

Referring to FIGS. 1-3 of the drawings, the illustrated artificial lung (oxygenator/heat-exchanger) 10 is generally cylindrical and comprises a central, generally cylindrical oxygenator unit designated generally by the reference numeral 12, a blood defoamer assembly 14 surrounding the oxygenator unit, an upper housing 16 and a lower housing 18. The space within lower housing 18 surrounding oxygenator unit 12 serves as a blood reservoir 20, and a heat-exchange unit designated generally by reference numeral 22 occupies substantially the entire lower portion of the blood reservoir.

Referring particularly to FIG. 3, oxygen-depleted venous blood, drained from the patient, generally under gravity, enters a mixing chamber 24 of oxygenator 12 through blood inlets 26. To aid in minimizing turbulence, a cylindrical, open cell foam baffle 27, preferably of polyurethane, preferably is located in the lower part of chamber 24. Oxygen is fed to mixing chamber 24 through oxygen inlet 28, diffuser chamber 30 and diffuser head 32. Diffuser head 32 comprises a plurality of uniformly spaced, tapered openings 34, which are, in the illustrated embodiment, of the order of 350 microns in diameter at the outer surface of diffuser heat 32.

The oxygen and blood are intimately admixed in the upper portion of mixing chamber 24 and flow together upwardly through a cylindrical oxygenation chamber 26 which contains a column of uniformly sized tightly packed, beads 38. Typically, beads 38 are about 8 mm. in diameter. Suitably, they may range in diameter from about 3 mm. to about 10 mm. or more. The beads are preferably made of polystyrene, but may be made of any suitable material, such as polyethylene, or polytetrafluoroethylene, which will not react with the blood and which will provide a hard, smooth surface. A pair of retainer caps 40, 41, having substantially uniformly distributed openings of a size sufficiently large to permit the passage of blood and oxygen therethrough but sufficiently small to retain the leads therebetween, are fitted at the top and bottom, respectively, of oxygenation chamber 36.

A detailed description of the oxygenation process that occurs in the bubble-type oxygenator described above is set forth in U.S. Pat. No. 3,898,045, issued Aug. 5, 1975 to Wallace W. Bowley, and will not be repeated here in detail. (See also "Bubble Mechanics an Oxygen Transfer, " G. L. Hammond and W. W. Bowley, J. Thorac. Cardiovasc. Surg., 71(3): 422–28, Mar., 1976, the contents of both of the foregoing being incorporated herein by reference). However, it should be understood that, during the upward movement of the oxygen and blood within chamber 36, the blood is oxygenated, carbon dioxide is removed therefrom and a foamed mixture of blood and gas is created. It is this foamed mixture, along with unfoamed oxygenated blood, released carbon dioxide and unused oxygen, that exits from the top of the chamber.

After exiting from the top of chamber 36, the oxygenated blood, carbon dioxide, unused oxygen, and foamed mixture pass into defoamer assembly 14 where the bood is separated from the gaseous components (defoamed).

Defoaming may be effected in any manner known to the art, for example, by causing the oxygenated, foam-containing blood to pass through a polyurethane foam 42 which is coated with a non-wetting or antifoaming agent or through a material which inherently has non-wetting, bubble collapsing properties. Other defoamers known in the art of defoaming blood may also be used.

Referring particularly to FIG. 3, the defoamer 42 comprises an open cell foam, preferably of polyethylene, coated with an antifoaming agent. Defoamer 42 surrounds oxygenator 12 in such a manner as to facilitate the flow of foamed blood therethrough as well as to assure the defoaming of the blood. The following medical grade antifoaming agents, which are suitable for coating defoamer 42, are available from the Dow Corning Corporation: (1) Medical Antifoam A Compound (Simethicone); (2) Medical Antifoam AF Emulsion; and (3) Medical Antifoam C Emulsion. Other antifoaming agents approved for medical use may also be used.

A cylindrical diverter 44 is secured to the central portion of the inside wall of upper housing 16, as by force fitting within annulus 46. The inner diameter of diverter 44 is greater than the outer diameter of oxygenator unit 12, and its lower edge 47 extends below the upper retainer cap 40 so as to direct the oxygenated blood into defoamer unit 14.

A set of tapered ribs 52 (see FIGS. 2 and 3) is fixed to and integral with the upper part of central cylindrical oxygenator housing 54. Defoamer assembly 14 is designed with open space 48 between defoamer 42 and the upper region of oxygenator housing 54. This design permits on-foamed blood to pass directly to the base of the defoamer without radial passage through the upper region of the defoamer. The foam is cut to form this cylindrical foam configuration. The foam material is held in place by nylon fabric cover sock 49 which in turn is held in place by nylon banding straps 50. As shown in FIG. 9, the outer surface of cylindrical defoamer 42 is preferably scalloped to form concave passages 51 to allow for passage of $O_2$ and $CO_2$ between defoamer 42 and cover sock 49. In the illustrated oxygenator construction, this defoamer design allows for adequate blood defoaming up to 6 liters/minute.

The foamed blood passes into defoamer 42 at the upper portion thereof, near edge 47 of diverter 44, and is retained in defoamer 42 as it passes radially and downwardly therethrough for a sufficient time to allow for adequate defoaming. With this design, most blood exits defoamer 42 below the blood level in the reservoir, keeping turbulence in the reservoir to a minimum. A suitable vent 60 is provided in the upper housing 16 for the venting of the gases (principally $CO_2$ and excess $O_2$) from defoamer assembly 14.

As previously mentioned and as best seen in FIG. 3, the admixing of the blood and oxygen occurs in mixing chamber 24, which is defined by diffuser head 32, lower retainer cap 41 and the circumferential inwardly convex portion 56 formed in the lower region of housing 54. Portion 56 also forms a seat for lower retainer cap 41, which in turn serves to separate beads 38 from mixing chamber 24. Thus, all of the essential elements of oxygenator unit 12 are located within central housing 54.

A flange 64 (see FIG. 2) is provided to accurately position housing 54 within lower housing 18. Flange 64 extends upwardly from the bottom of the housing around the bottom of diffuser chamber 30 and has an outside diameter slightly smaller than the inside diameter of the lowermost edge of housing 54. In addition, both parts have inwardly extending shoulders 63 and 62, respectively, which mate to provide means for preventing relative rotational movement between lower housing 18 and oxygenator housing 54. As will be discussed in greater detail hereinafter, the mating configuration of the lower part of housing 54 and flange 64 are important structural features to maximize the efficiency of the heat-exchanger of the present invention.

As previously stated, heat-exchange unit 22 is designed to occupy substantially the entire lower portion of blood reservoir 20. To accomplish this, unit 22 is constructed from a vertically stacked array of individual coils 66 formed from continuous tubing. The tubing is wound in a spiral whose pitch is such as to provide a free space between convolutions of each coil of about 1/32 inch (0.79 mm.).

Since the limiting factor in the efficiency of the heat-exchanger of the subject invention is the heat transfer coefficient of the blood film, and not that of the material of which the heat-exchange coils 66 are fabricated, substantially any fluid impervious material which is compatible with both blood and the heat-exchange fluid may be employed. Suitable examples of such material include stainless steel, polypropylene, polyester, polyethylene, polystyrene, polytetrafluoroethylene and polyurethane. In a presently preferred embodiment, the coils are constructed of polyethylene tubing having an outer diameter of about 0.25 inch (0.635 cm.) and a wall thickness of about 0.02 inch (0.05 cm.). The thickness and diameter of the tubing may be varied as desired and will depend on the material of construction, but the thickness should be sufficient to withstand water pressure of the order of at least about 25 p.s.i. (1,760 g./cm.$^2$). A suitable range of tubing diameter for the presently preferred (high density) polyethylene tubing is an outer diameter of from about 0.125 inch (0.315 cm.) to about 0.5 inch (1.27 cm.), while wall thickness is desirably between about 0.01 inch (0.025 cm.) and about 0.025 inch (0.0635 cm.).

As shown in FIGS. 2–6, risers 68 and 70 lead from the flat, substantially horizontal coils 66 to heat-exchange fluid inlet and outlet manifolds 72 and 74, respectively, located externally of the interface between housings 16 and 18 of artificial lung 10. Thus, as best shown in FIGS. 1–3, housings 16 and 18 are separated by a spacer ring 76 and are provided, at their open, mating ends, with outwardly projecting rims 78 and 80, respectively. Spacer ring 76 forms a resilient gasket between the housings and is preferably made from a blood compatible material, such as silicone rubber.

Sets of ears 82a extend outwardly from upper housing 16, and downwardly opening notches 83a are provided in the ends of the ears for receiving the upper edges of manifolds 72 and 74. Similar ears 82b extend outwardly from lower housing 18 and have upwardly opening notches 83b for receiving and mating with the lower edges of the manifolds.

Manifolds 72 and 74 are essentially identical in construction and are adapted to receive the ends of risers 68 and 70, respectively. The risers pass through openings 90 formed in a generally axial direction through the wall of spacer ring 76, and each riser is secured and sealed at its end to a fitting 92 (FIG. 8) attached to its respective manifold. Referring to FIG. 8, a riser 70 is shown secured firmly at its end 70a, within fitting 92 which is, in turn, integrally connected to manifold 74. Fitting 92 includes a threaded male boss 92 secured to the manifold, an internally threaded mating female lock nut 94 and an O-ring 95 positioned between boss 93 and lock nut 94. O-ring 95 is designed to contract radially inwardly when lock nut 94 is turned relative to boss 93 to securely clamp riser end 70a within fitting 92 and to form a seal around the periphery of the riser. As stated above, all risers 68 and 70 are similarly secured to their respective manifold at a location external from housings 16 and 18.

Manifolds 72 and 74 have a plurality of apertures 96 (see FIG. 6) through which risers 68 and 70 communicate with the central manifold chambers 97 and 98, respectively. Manifold chambers 97 and 98 have suitable fittings 100 and 101, respectively, in the lower wall thereof, that may function as either an inlet or an outlet fitting. As described herein, manifold 72 has been designated as the "inlet" manifold and manifold 74 has been designated as the "outlet" manifold. If desired, the flow of heat-exchange fluid may be reversed in this unique heat-exchange unit and the manifold designations would, thus, also be reversed.

As best seen in FIGS. 1 and 2, in the assembly of the apparatus, rims 78 and 80 are brought together with spacer ring 76 therebetween, and a plurality of clips 84 are positioned around the periphery of the assembly within notches 85 to thereby firmly clamp the three components together.

As was indicated earlier, each coil 66 together with its associated inlet riser 68 and outlet riser 70 is made of a single, continuous length of tubing, and all connections between the tubing and manifolds 72 and 74 are external to housings 16 and 18, thereby virtually eliminating the possibility of a leak of heat-exchange fluid within heat-exchanger 22. Rather, if any leak were to occur, it would be at the external connections of risers 68 and 70 to manifolds 72 and 74, where such leak would be readily detectable and correctable, and where there would be no danger of the heat-exchange fluid contacting the blood and thus injuring the patient, perhaps fatally.

As already indicated, oxygenated blood from defoamer 14 flows downwardly through reservoir 20 over coils 66 and through the spaces therebetween. By virtue of the spacing of coils 66 and the complementary associated configuration of housings 18 and 54 at shoulders 62 and 63, the blood surrounding these coils is maintained in a uniform, thin film, promoting uniform, effective heat exchange between the coils and the blood.

Depending upon the flexibility of the tubing used in the contruction of coils 66, it may be desirable to provide means for maintaining the spacing between adjacent coils and between adjacent convolutions in each coil. Any suitable means, such as clips, may be used for this purpose so long as the chosen means is made from a blood compatible material.

As a further means for eliminating open space within blood reservoir 20 and for preventing the displacement of coils 66 within housing 18, the curvature of risers 70 at the juncture of the risers and their associated coils 66 (see FIG. 2) is designed to mate with a shoulder 105 (FIG. 2) formed in the wall of lower housing 18. This is a further means for assuring that heat exchanger 22 which occupies a substantial portion of reservoir 20, is securely positioned therein.

The oxygenated blood, at the desired temperature, exits artificial lung 10 through arterial ports 88 (FIG. 3) and thence is returned to the patient through suitable conduit means (not shown) and, if desired, intermediate other devices such as one or more filters.

Any suitable heat-exchange medium may be employed in heat-exchanger 22. Generally, however the medium of choice is a mixture of hot and cold tap water which is preferably fed through an adjustable, calibrated mixing valve (not shown) that controls the heat-exchanger fluid temperature and is set to cut off the fluid supply to inlet manifold 72 if its temperature exceeds about 42° C. Outlet manifold 74 is connected to a waste drain, although, is desired, the heat-exchange fluid could be recirculated.

Housings 16, 18 and 54 may be molded of a blood compatible synthetic polymer such as those listed above or of any other suitable blood compatible material, a presently preferred material being polycarbonate. A suitable handle 107 is formed integral with upper housing 16 to provide a convenient means for transporting and supporting the unit after it has been fully assembled.

Variations can, of course, be made without departing from the spirit and scope of the invention.

What is claimed is:

1. A blood treatment apparatus comprising: an upper housing; a lower housing; a substantially cylindrical central housing supported at one end on the bottom wall of said lower housing and defining a blood oxygenation chamber therewithin; blood inlet means in said bottom wall for feeding blood to said central housing; oxygen inlet means in said bottom wall for feeding oxygen to said central housing; a blood reservoir in the lower portion of said lower housing surrounding said central housing for receiving oxygenated blood from said oxygenation chamber; blood outlet means in said bottom wall external of said central housing in communication with said blood reservoir for feeding oxygenated blood from said reservoir; a plurality of closely spaced heat-exchange coils located in said blood reservoir for regulating the temperature of said oxygenated blood; and an annular gasket separating said upper and lower housings and forming a seal therebetween; said coils having inlet and outlet ends extending through openings in said gasket.

2. The blood treatment apparatus of claim 1 wherein said gasket is located approximately midway between the bottom all of said lower housing and the top wall of said upper housing and said hollow tubes extend upwardly from said coils through said openings in said gasket to form risers between said coils and the inlet and outlet ends of said tubes.

3. The blood treatment apparatus of claim 2 wherein the inlet ends of said tubes are all connected to an inlet fluid manifold external of said upper and lower housings and the outlet ends of said tubes are all connected to an outlet fluid manifold external of said upper and lower housings.

4. The blood treatment apparatus of claim 3 wherein the side wall of said lower housing and the wall of said central housing have shoulders in contact with at least one of said risers for accurately positioning and maintaining said coils within said lower housing and for maintaining uniform spacing between said coils and said housings.

5. The blood treatment apparatus of claim 3 wherein the distance between each convolution is approximately 1/32 inch and the vertical distance between adjacent coils is approximately 1/32 inch.

6. The blood treatment apparatus of claim 1 wherein said coils are formed of continuous hollow tubes.

7. The blood treatment apparatus of claim 6 wherein the coils are arranged in a vertically stacked array with each coil positioned in a substantially horizontal plane within said reservoir.

8. The blood treatment apparatus of claim 7 wherein each coil occupies a substantial portion of the area of said reservoir within its respective horizontal plane.

9. The blood treatment apparatus of claim 8 wherein each coil is spirally wound with uniform spacings between convolutions.

10. The blood treatment apparatus of claim 9 wherein the other end of said central housing extends vertically upwardly within said upper housing to a location slightly spaced from the top wall of said upper housing and said apparatus further comprises defoaming means surrounding the upper portion of said central housing for defoaming the oxygenated blood as it exits from the top of said blood oxygenation chamber.

* * * * *

UNITED STATES PATENT AND TRADEMARK OFFICE
CERTIFICATE OF CORRECTION

PATENT NO. : 4,160,801

DATED : July 10, 1979

INVENTOR(S) : Anthony Badolato, Joseph S. Farrell

It is certified that error appears in the above-identified patent and that said Letters Patent are hereby corrected as shown below:

Column 7, line 6: "all" should be --wall--.

Signed and Sealed this

Ninth Day of June 1981

[SEAL]

Attest:

RENE D. TEGTMEYER

Attesting Officer

Acting Commissioner of Patents and Trademarks